(12) United States Patent
Carter et al.

(10) Patent No.: US 10,046,155 B2
(45) Date of Patent: *Aug. 14, 2018

(54) LUER CONNECTOR

(71) Applicant: Becton, Dickinson and Company, Franklin Lakes, NJ (US)

(72) Inventors: Jeffery Lee Carter, Pleasant View, UT (US); Cameron James Nielsen, San Diego, CA (US); Bart David Peterson, Farmington, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 103 days.

This patent is subject to a terminal disclaimer.

(21) Appl. No.: 15/191,215

(22) Filed: Jun. 23, 2016

(65) Prior Publication Data

US 2016/0296742 A1   Oct. 13, 2016

Related U.S. Application Data

(63) Continuation of application No. 13/185,146, filed on Jul. 18, 2011, now Pat. No. 9,381,337.

(Continued)

(51) Int. Cl.
*A61M 39/10* (2006.01)
*A61M 5/00* (2006.01)
*A61M 39/02* (2006.01)

(52) U.S. Cl.
CPC ........ *A61M 39/1011* (2013.01); *A61M 5/007* (2013.01); *A61M 39/02* (2013.01);
(Continued)

(58) Field of Classification Search
CPC .. A61M 39/10; A61M 39/1011; A61M 5/007; A61M 2205/583; A61M 2205/584;
(Continued)

(56) References Cited

U.S. PATENT DOCUMENTS

| 4,230,109 A | 10/1980 | Geiss |
| 4,369,781 A | 1/1983 | Gilson et al. |
| 5,489,275 A | 2/1996 | Thompson et al. |
| 5,620,427 A | 4/1997 | Werschmidt et al. |
| 5,984,373 A | 11/1999 | Fitoussi et al. |
| D625,003 S | 10/2010 | Stephens |
| 9,381,337 B2 * | 7/2016 | Carter ................... A61M 5/007 |
| 2004/0201216 A1 | 10/2004 | Segal et al. |
| 2007/0088327 A1 | 4/2007 | Guala |
| 2007/0129705 A1 | 6/2007 | Trombley et al. |

(Continued)

FOREIGN PATENT DOCUMENTS

| AU | 2011282264 | 2/2013 |
| CN | 1931388 A | 3/2007 |

(Continued)

*Primary Examiner* — Nathan R Price
*Assistant Examiner* — Anh Bui
(74) *Attorney, Agent, or Firm* — Kevin Stinger; Craig Metcalf; Kirton McConkie

(57) ABSTRACT

A luer lock connector is disclosed. The luer lock connector includes a connector body having a distal end, a proximal end, and a gripping portion between the distal end and the proximal end. A substantially flexible material is disposed on at least the outer surface of the gripping portion of the connector body. An intravenous line is coupled to the distal end of the connector body. A luer connector fitting is disposed on the proximal end of the body, the luer connector having an outer diameter less than a maximum exterior thickness of the gripping portion of the connector body.

20 Claims, 9 Drawing Sheets

Related U.S. Application Data

(60) Provisional application No. 61/365,406, filed on Jul. 19, 2010.

(52) U.S. Cl.
CPC ....... *A61M 39/10* (2013.01); *A61B 2562/225* (2013.01); *A61M 2039/0258* (2013.01); *A61M 2039/0273* (2013.01); *A61M 2039/0276* (2013.01); *A61M 2039/1077* (2013.01); *A61M 2205/3368* (2013.01); *A61M 2205/583* (2013.01); *A61M 2205/586* (2013.01); *A61M 2205/6063* (2013.01)

(58) Field of Classification Search
CPC .... A61M 2205/586; A61M 2205/6063; A61M 2205/6072; A61M 2205/6081; A61M 2039/1027; A61M 2039/1077; A61B 2562/225
See application file for complete search history.

(56) References Cited

U.S. PATENT DOCUMENTS

| | | |
|---|---|---|
| 2007/0224865 A1 | 9/2007 | Fangrow |
| 2010/0004634 A1 | 1/2010 | Whitley |

FOREIGN PATENT DOCUMENTS

| | | |
|---|---|---|
| EP | 1 747 797 A1 | 1/2007 |
| EP | 2595690 | 11/2016 |
| JP | 2005-501616 A | 1/2005 |
| JP | 2008-518719 A | 6/2008 |
| JP | 5984807 | 9/2016 |
| WO | 2006/052655 A2 | 5/2006 |
| WO | 2012/012402 | 1/2012 |

\* cited by examiner

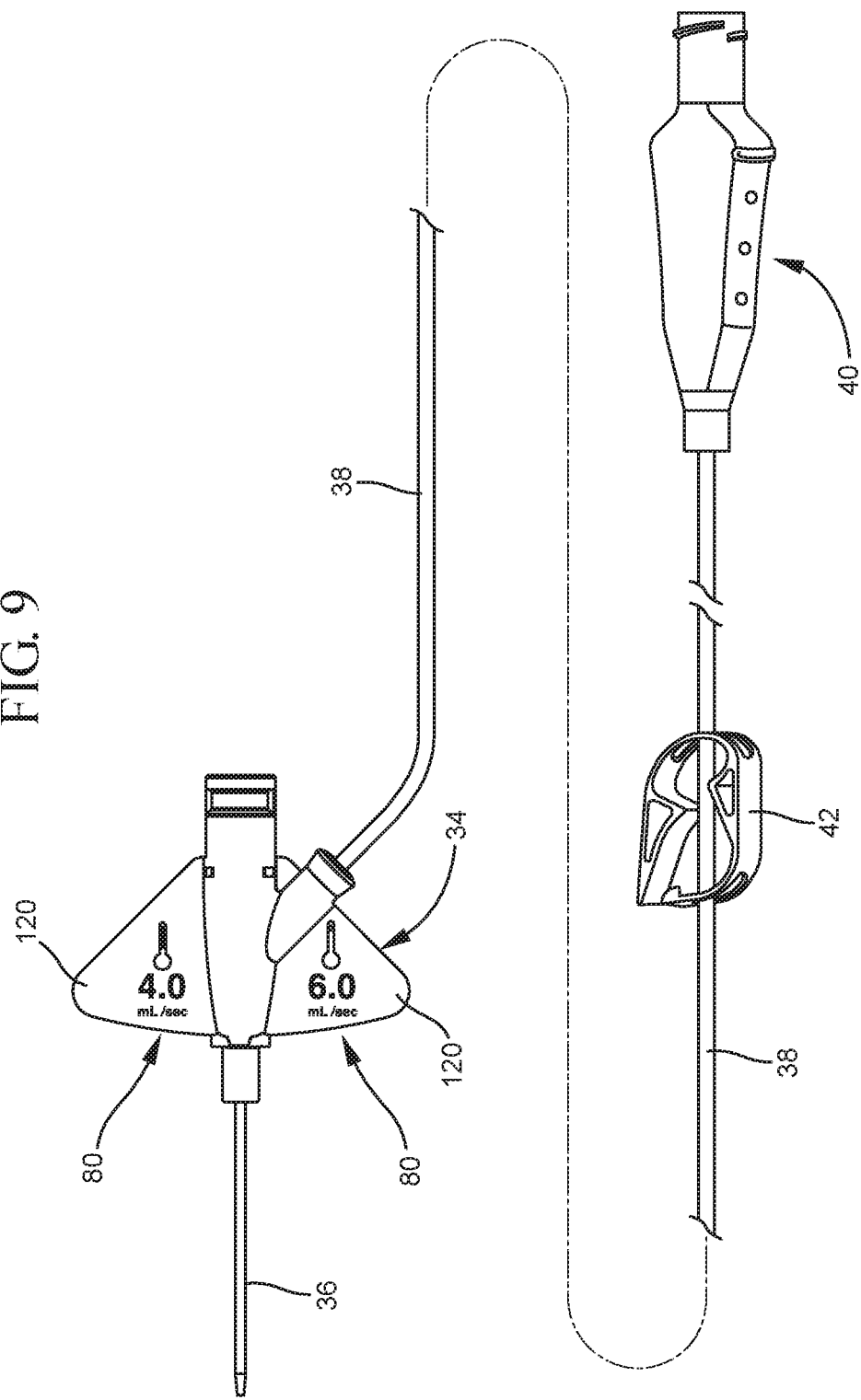

LUER CONNECTOR

RELATED APPLICATIONS

This application is a continuation of U.S. patent application Ser. No. 13/185,146, filed Jul. 18, 2011, and titled LUER CONNECTOR, which claims the benefit of U.S. Provisional Application No. 61/365,406 filed Jul. 19, 2010, entitled LUER HUB OR DEVICE FOR HIGH PRESSURE INJECTION ERGONOMIC DESIGN WITH DISPLAYED INFORMATION (FLOW RATE, ETC), and are incorporated herein by reference.

BACKGROUND

Vascular access devices are used for communicating fluid with the anatomy of a patient. For example, vascular access devices, such as catheters, are commonly used for infusing fluid, such as saline solution, various medicaments, and/or total parenteral nutrition, into a patient, withdrawing blood from a patient, and/or monitoring various parameters of the patient's vascular system.

A variety of clinical circumstances necessitate that fluid be injected intravenously into a patient by a specialized "power injector" pump intravenously at very high flow rates. The power injector pump may establish a bolus, or small plug of fluid, in the bloodstream of the patient. In some circumstances, a high contrast media is used as the infusant in order produce a bolus that can be imaged via imaging techniques. Power injection procedures generate high pressures within the infusion system, thereby requiring some specialized vascular access devices, extension sets, media transfer sets, pump syringes, and bulk or pre-filled contrast media syringes. A current trend in healthcare is to increase the fluid density of the infusant.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 20 ml/second is needed to ensure sufficient bolus concentration. Power injections of viscous media at this injection rate produce significant back pressure within the infusion system that commonly results in a failure of the infusion system components.

FIG. 1 depicts a prior art luer connector 240 that forms part of a connection that can fail during power injector procedures. The luer connector 240 forms a connection with a coupler 30 as part of an infusion system that introduces fluid through an extension set 26 across this connection and into an extension tube 38 leading to a catheter adapter or other such device. The luer connector 240 may include wings 242 and/or rounded protrusions 244 for assisting a user to grip and twist the luer port 240. The proximal end of the luer connector 240 includes a luer connector fitting 72 with luer threads 74 that interlock with corresponding threads 254 within the coupler 30.

As illustrated in FIGS. 1 to 3, the prior art luer connector 240 may fail if used improperly. FIG. 1 depicts the relative proportions of the luer port an index finger 260 (that is approximately 0.75 inches across) of an adult hand. As can be seen, the index finger 260 is substantially larger than the luer connector 240 even when considering the wings 242 of the luer port. The length 55 of the luer connector 240 is less than or equal to about 0.8 inches, the thickness 62 is less than or equal to about 0.17, and the maximum span 246 of the wings is less than or equal to about 0.34 inches. As can be seen, the length 56 of the grippable portion of the body of the luer connector 240 is less than the length of the entire luer port 240, since the luer connector fitting 72 cannot be gripped during operation since it will be covered by the coupler 30. The coupler 30 has a length 250 and a representative depth 252, which represents the optimal depth of the luer connector fitting 72 when it is fully interlocked within the coupler 30.

FIG. 2 illustrates one problem that can occur during the set-up of the luer connector 240. As depicted, the luer connector 240 may be gripped between an index finger 260 and a thumb 262 of a user. As shown, the luer connector 240 is gripped in a manner that allows a user twisting leverage, with the fingers 260, 262 on the grippable portion of luer port 240 and winds 242. One of the challenges with this luer connector 240 is shown in FIG. 3, wherein when the coupler 30 is advanced over the luer connector fitting 72 and interlocked thereon the user's fingers 260, 262 get in the way and contact the coupler 30 at one or more points 270. At this instance, the user can naturally assume that the coupler 30 and the luer connector 240 are sufficiently interlocked. This assumption may be strengthened by the fact that the resistance to turning can increase proportionally as the luer connector 240 is advanced into coupler 30. This increased resistance combined with the coupler contacting the user's fingers 260, 262 can trigger the user to believe that the connection is secured. The increasing resistance also places pressure on the user's fingers which may feel pain when twisting against the hard material of the connector. However, as shown, in many instances, the luer connector 240 must be advanced an additional distance 256 before it is fully secured to the coupler 30. This final advancement can be difficult and even painful to the user's fingers. In high pressure injection systems, an incomplete connection, such as that shown in FIG. 3 can result in results in a failure of the infusion system or complications, including leaking, a decrease in pressure, disconnection, and contamination.

Additionally, problems may occur when the power injector is programmed to infuse fluids at rates that are too higher for the system components. During power injection procedures, a high-pressure injector is programmed with a maximum flow rate in order to maintain the infusion rate under this maximum value. This maximum limit protects the patient as well as vascular access devices, such as catheter adapters, connected to the power injector. Many, if not all, vascular access devices used in power injection procedures are manufactured to withstand flow rates up to a maximum value. This maximum value is generally included in the vascular access device's published and/or marketing literature, and often provides different maximum values based on the temperature of the infusant. For example, some catheter assemblies are manufactured to infuse a room temperature infusant at a rate of 4 mL/s and a warmed infusant (warmed to the patient's body temperature) at a rate of 6 mL/s. A clinician who programs the maximum flow rates into the power injector system must be aware of the maximum values so that he does correctly programs the power injector. In some past instances, clinicians have not been aware of these values and problems have occurred.

SUMMARY

A connector and catheter adapter is presented that has been developed in response to problems and needs in the art that have not yet been fully resolved by currently available systems. Specifically, a connector is shaped and sized to be ergonomic and provide room for a user's finger in a manner that does not interfere with a proper connection. Furthermore, the connector can include a flexible material that is softer on the user's hands and can provide greater grip and additional user comfort. The connector can also be made larger to provide significantly more leverage facilitating proper connections. The connector may also include clearly visible text that indicates the maximum flow rates for the connector and a down line catheter adapter. Since clinicians must connect the connector with its down line catheter adapter to the power injector, the connector provides an appropriate location to label the maximum flow rates of the catheter adapter. Providing this information to a clinician can encourage proper infusant rates, which will result in fewer complications involving instruments and patient injuries.

In one aspect of the invention, a luer lock connector comprises: a connector body having a distal end, a proximal end, and a gripping portion between the distal end and the proximal end; a substantially flexible material disposed on at least the outer surface of the gripping portion of the connector body; an intravenous line coupled to the distal end of the connector body; and a luer connector disposed on the proximal end of the body, the luer connector having an outer diameter less than a maximum exterior thickness of the gripping portion of the connector body.

Implementations of the present invention may include one or more of the following features. A substantially rigid material may form an inner portion of the connector body and may also form the luer connector fitting. The maximum exterior thickness of the gripping portion may be greater than or equal to 0.2 inch. The connector body may a length greater than or equal to 1.1 inch. The connector body may form a single port connector. A label may be disposed on an exterior surface of the connector body. The label may have text that conveys information relating to a product specification of the luer lock connector or to a down line vascular access device. The text may have a text size of 12 point font or larger. The intravenous line may be further coupled to a catheter adapter. The catheter adapter may have a label disposed on an exterior surface of the catheter adapter. The label may have text that conveys information relating to a product specification of the catheter adapter. The gripping portion of the connector body may include ergonomic grip indents on opposing sides of the connector body. The ergonomic grip indents may include one or more gripping features. A grip shield may be interposed between the gripping portion and the luer connector. The outer surface of the gripping portion of the connector body may taper from a larger proximal portion to a smaller distal portion. The outer surface of the gripping portion may be substantially disk-shaped.

In another aspect, a luer lock connector comprises: a connector body having a distal end, a proximal end, and a gripping portion between the distal end and the proximal end; an intravenous line coupled to the distal end of the connector body; a luer connector disposed on the proximal end of the body; a substantially rigid material forming the single port of the connector body and an inner portion of the connector body; and a flexible material forming at least an outer portion of the gripping portion of the connector body.

Implementations of the present invention may include one or more of the following features. The flexible material may be over molded over the rigid material. The gripping portion may have a maximum thickness greater than the outer thickness of the luer connector fitting. The maximum thickness may be equal to or greater than 0.2 inches. The gripping portion may further have a maximum length equal to or greater than 1.1 inch. The gripping portion of the connector body may include ergonomic grip indents on opposing sides of the connector body. A grip shield may be interposed between the gripping portion and the luer connector.

In another aspect, a luer lock connector comprises: a connector body having a distal end, a proximal end, and a gripping portion between the distal end and the proximal end, the connector body forming a single port connector; an intravenous line coupled to the distal end of the connector body; a luer connector disposed on the proximal end of the body, the luer connector having an outer diameter less than a maximum exterior thickness of the gripping portion of the connector body, the maximum thickness being equal to or greater than 0.2 inch, the gripping portion further having a maximum length equal to or greater than 1.1 inch; a grip shield interposed between the gripping portion of the connector body and the luer connector; a first material forming the single port of the connector body and an inner portion of the connector body, the first material being substantially rigid; a second material forming at least an outer portion of the gripping portion of the connector body, the second material being compressible; and a label disposed on an outer surface of the connector body, the label having text that conveys information relating to a product specification of the luer lock connector or to a down line device.

Implementations of the present invention may include one or more of the following features. The text may have a text size of 12 point font or larger. The outer surface of the gripping portion of the connector body may taper from a larger proximal portion to a smaller distal portion. The down line device may be a catheter adapter coupled to the intravenous line.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 9 is a perspective view of an infusion system with a catheter adapter having a label in accordance with representative embodiments of the present invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
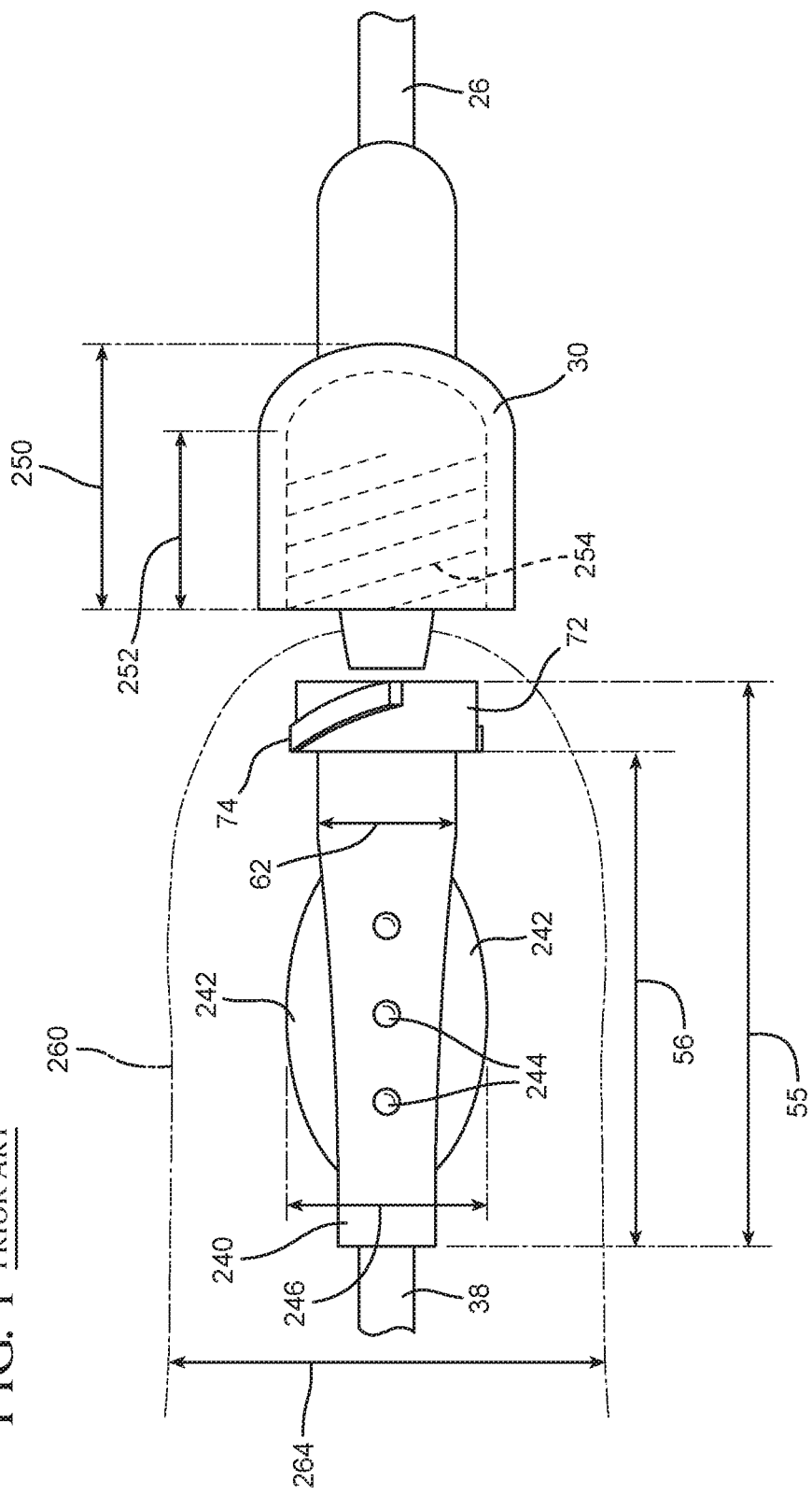
FIG. 1 is a perspective view of prior art luer connector and coupler.
Figure 2:
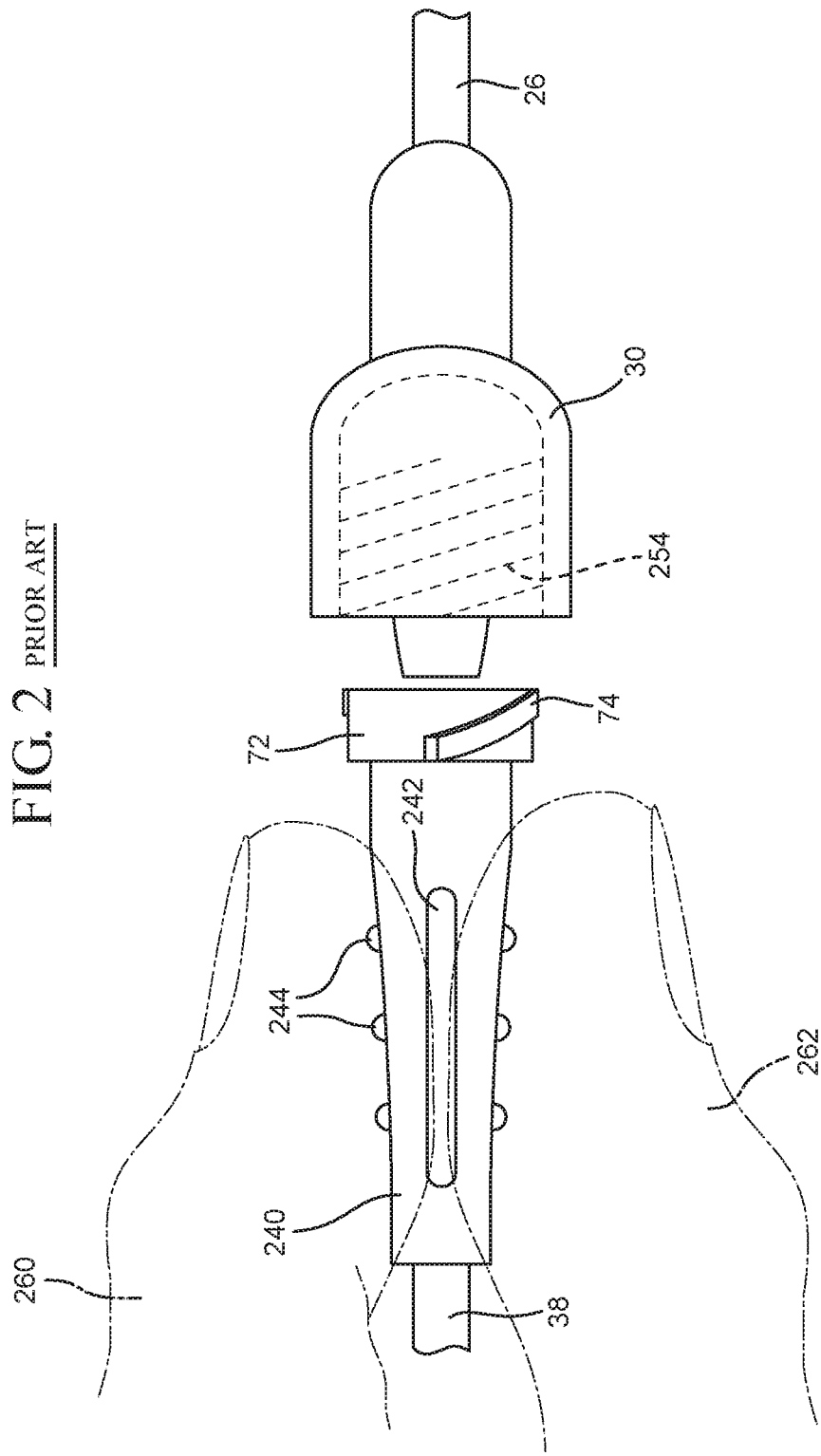
FIG. 2 is another perspective view of the prior art luer connector of FIG. 1 within a user's fingers.
Figure 3:
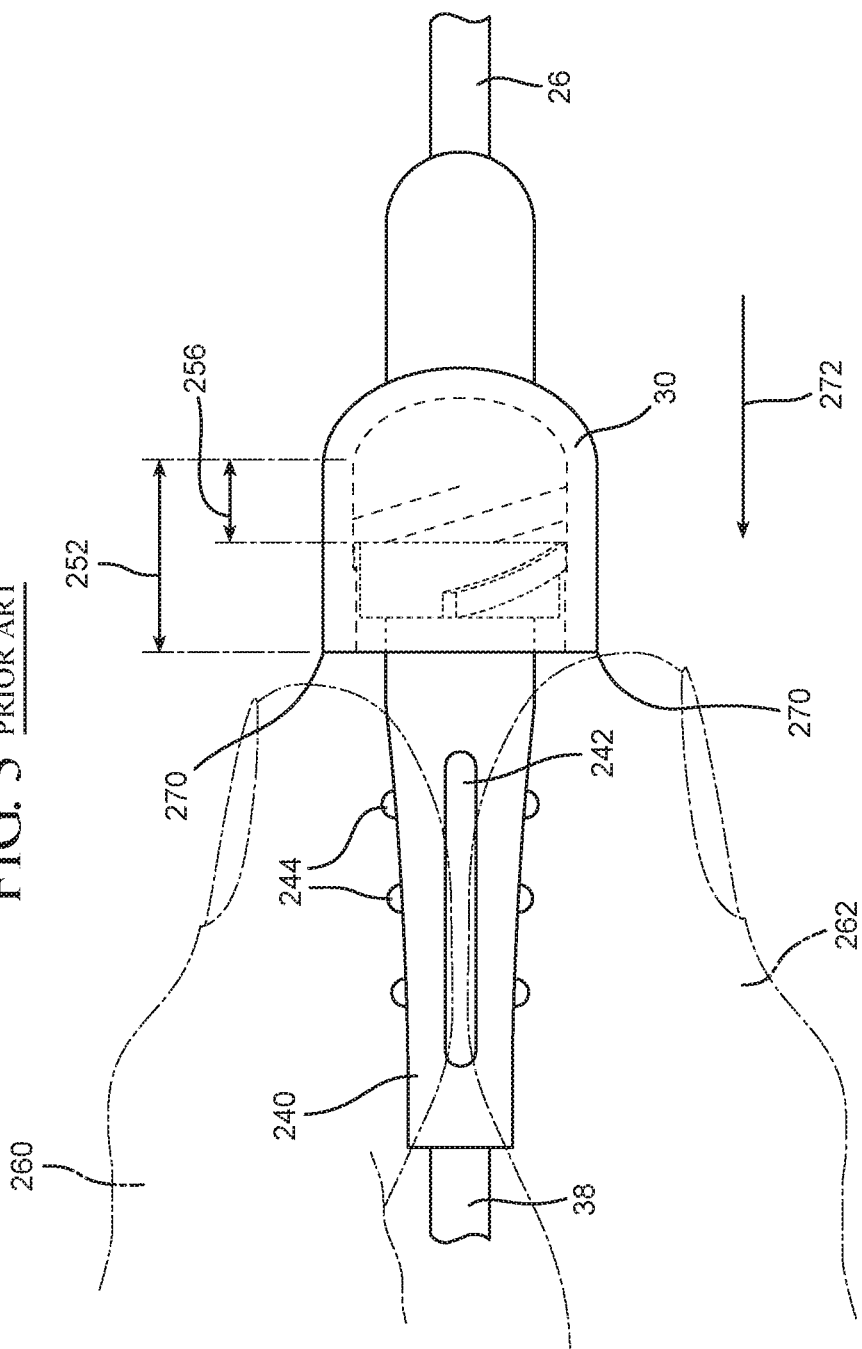
FIG. 3 is another perspective view of a prior art luer connector of FIGS. 1 and 2 within a user's fingers while it is connected to the coupler.
Figure 4:
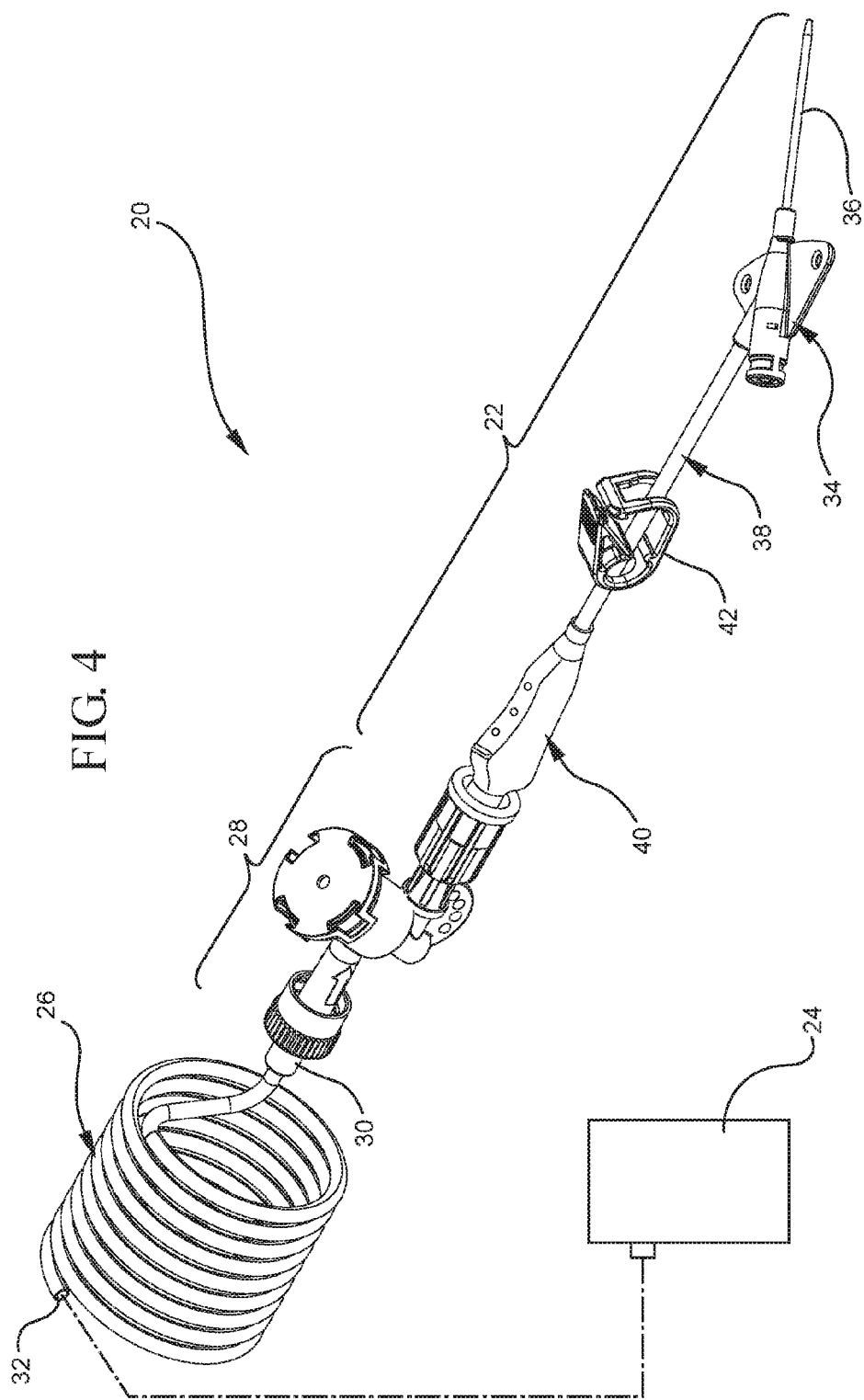
FIG. 4 is a perspective view of an infusion system in accordance with representative embodiments of the present invention.

Reference will now be made to FIG. 4, which depicts a vascular infusion system 20, in accordance with representative embodiments. Infusion systems of this type are commonly configured to operate at internal pressures up to, for example, about 2000 psi. Many systems operate in the range of 75 to 2000 psi or more, while specific devices of this type operate at 100, 200, and 300 psi. The vascular infusion system 20 comprises a vascular access device 22 coupled to an injector pump 24 via a coiled extension set 26. In some embodiments, the vascular infusion system 20 further comprises a safety device 28 positioned between the vascular access device 22 and the injector pump 24. In some embodiments, a safety device 28 is provided to automatically occlude the fluid path of the vascular infusion system 20, thereby preventing excessive pressure buildup in downstream infusion components.

An injector pump 24 generally comprises a fluid pumping apparatus configured to rapidly deliver an infusant, such as blood, medicaments, and CT scan contrast agents to a patient's vascular system. Desirable infusants may also include various fluids of high viscosity as required for medical and diagnostic procedures. In some embodiments, the injector pump 24 comprises a power injector capable of delivering an infusant to a patient at flow rates from about 10 mL/hour up to about 1200 mL/minute. In some embodiments, a high infusion flow rate is desirable for medical procedures which require enhanced bolus density of an infusant in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 24 and a vascular access device 22 are selected to compatibly achieve a desired infusion flow rate.

A coiled extension set 26 generally comprises flexible or semi-flexible polymer tubing configured to deliver an infusant from the injector pump 24 to the vascular access device 22. The coiled extension set 26 includes a first coupler 30 for connecting the coiled extension set 26 to a downstream device. The coiled extension set 26 also includes a second coupler 32 for connecting the coiled extension set 26 to the injector pump 24. A coiled configuration of the coiled extension set 26 generally prevents undesirable kinking or occlusion of the coiled extension set 26 during infusion procedures. However, one of skill in the art will appreciate that the coiled extension set 26 may include any configuration capable of efficiently delivering an infusant from an injector pump 24 to the patient via a vascular access device 22. In some embodiments, the coiled extension set 26 is coupled between a syringe and a vascular access device whereby an infusant is manually injected into a patient. In other embodiments, the infusion system comprises only a syringe and a vascular access device, in accordance with the present invention.

The vascular access device 22 generally comprises a peripheral intravenous catheter adapter 34. A peripheral intravenous catheter adapter 34 in accordance with the present invention generally comprises a short or truncated catheter 36 (usually 13 mm to 52 mm) that is inserted into a small peripheral vein. Such catheters 36 generally comprise a diameter of approximately a 14 gauge catheter or smaller. Peripheral intravenous catheter adapters 34 are typically designed for temporary placement. The short length of the catheter 36 facilitates convenient placement of the catheter 36 but makes them prone to premature dislodging from the vein due to movement of the patient and/or recoil forces experienced during infusion procedures.

A desired infusant is typically delivered to the catheter adapter 34 from the injector pump 24 via a section of intravenous (IV) tubing 38 coupled to the catheter adapter 34. In some embodiments, a connector 40 is coupled to an end of the IV tubing 38 opposite the catheter adapter 34, enabling the vascular access device 22 to be coupled to the remainder of the vascular infusion system 20. In some instances, a clamp 42 is disposed on the IV tubing 38 to enable a clinician to manually stop the flow of fluid through the IV tubing 38. One of skill in the art will appreciate the possible variations and specific features of available infusion systems and vascular access devices 22, as are commonly used in the medical and research professions. For example, in some embodiments a catheter adapter 34 may include additional or alternative access sites, clamps, parallel intravenous lines, valves, couplers, introducer needles, coatings, and/or materials as desired to fit a specific application.

Figure 5:
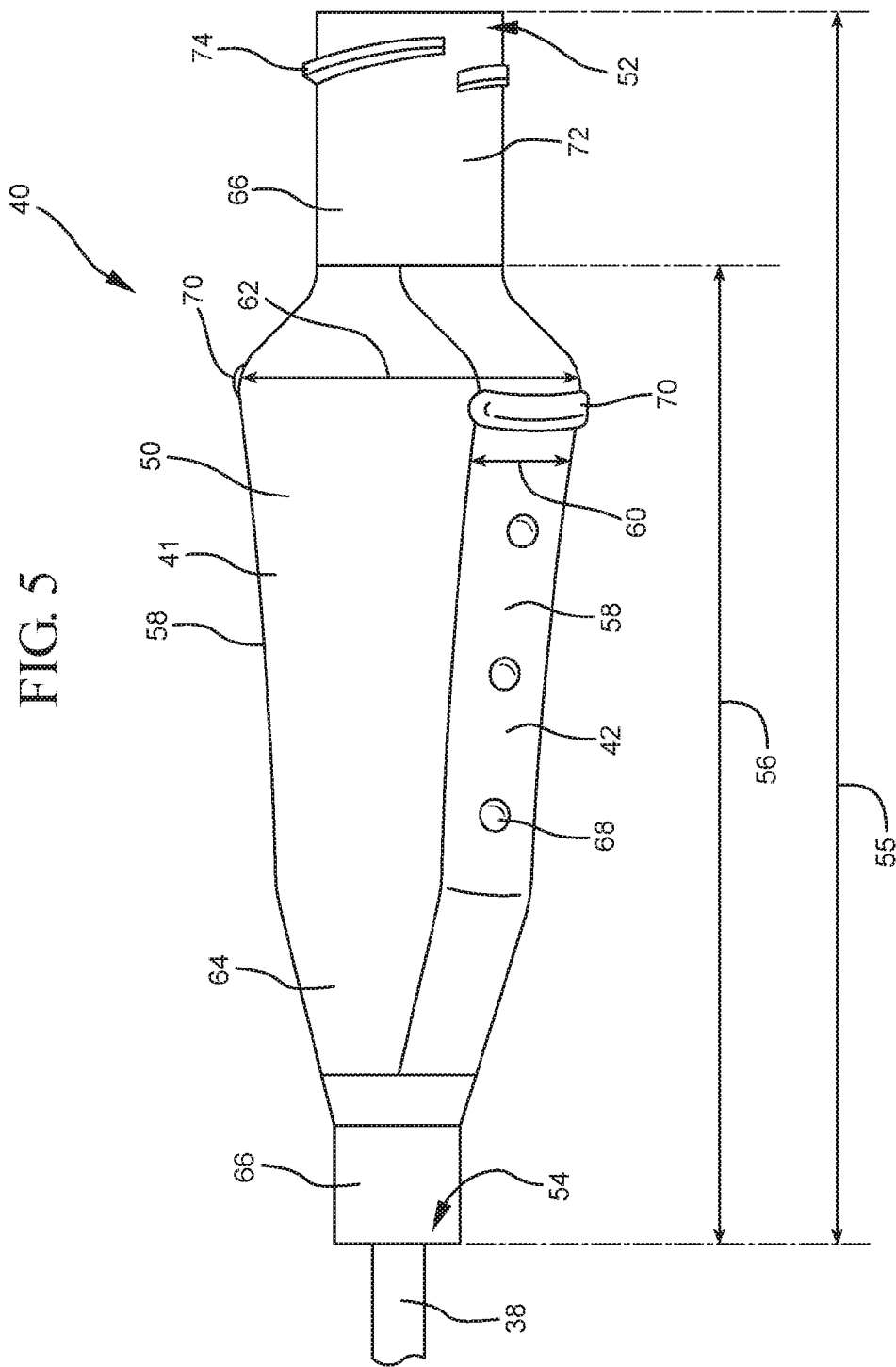
FIG. 5 is a perspective view of a luer connector in accordance with representative embodiments of the present invention.

Reference will now be made to FIG. 5, which depicts a luer lock connector (or luer connector) 40 having a connector body 41 with a grip portion 50 large enough or larger than necessary to be securely gripped by the fingers of the average adult. This size is larger than traditional luer connectors which generally have smaller dimensions, such as a length of about 0.8 inches and maximum exterior thickness of a grip portion 50 of about 0.17 inches. In contrast, in non-limiting embodiments of the present luer connector 40, the length 56 of the grip portion 50 of the connector body 41 is between about 0.6 and 2.0 inches. In other embodiments, the length 56 of the grip portion 50 of the connector body 41 is between about 0.8 and 1.8 inches. In still other embodiments, the length 56 of the grip portion 50 of the connector body 41 is between about 1.1 and 1.4 inches. Additionally, in some configurations, the length 55 of the entire luer connector 40 is between about 1.3 and 1.8 inches. In other configurations, the length 55 of the entire luer connector 40 is between about 1.5 and 1.6 inches Similarly, the maximum exterior thickness 62 of the grip portion 50 (which does not include the added dimension of any wings or narrow protrusions from the main body) can be sized to be firmly gripped by a user. The maximum exterior thickness 62 is the maximum distance between exterior surfaces of the connector body 41 when taken as a cross section that is normal to the longitudinal axis of the luer connector 40. Accordingly, in some embodiments, the maximum exterior thickness 62 of the grip portion 50 is between about 0.2 and 0.6 inches. In other embodiments, the maximum thickness 62 or the grip portion 50 is between about 0.2 and 0.4 inches. In yet other embodiments, the maximum thickness 62 or the grip portion 50 is between about 0.23 and 0.3 inches.

Figure 7:
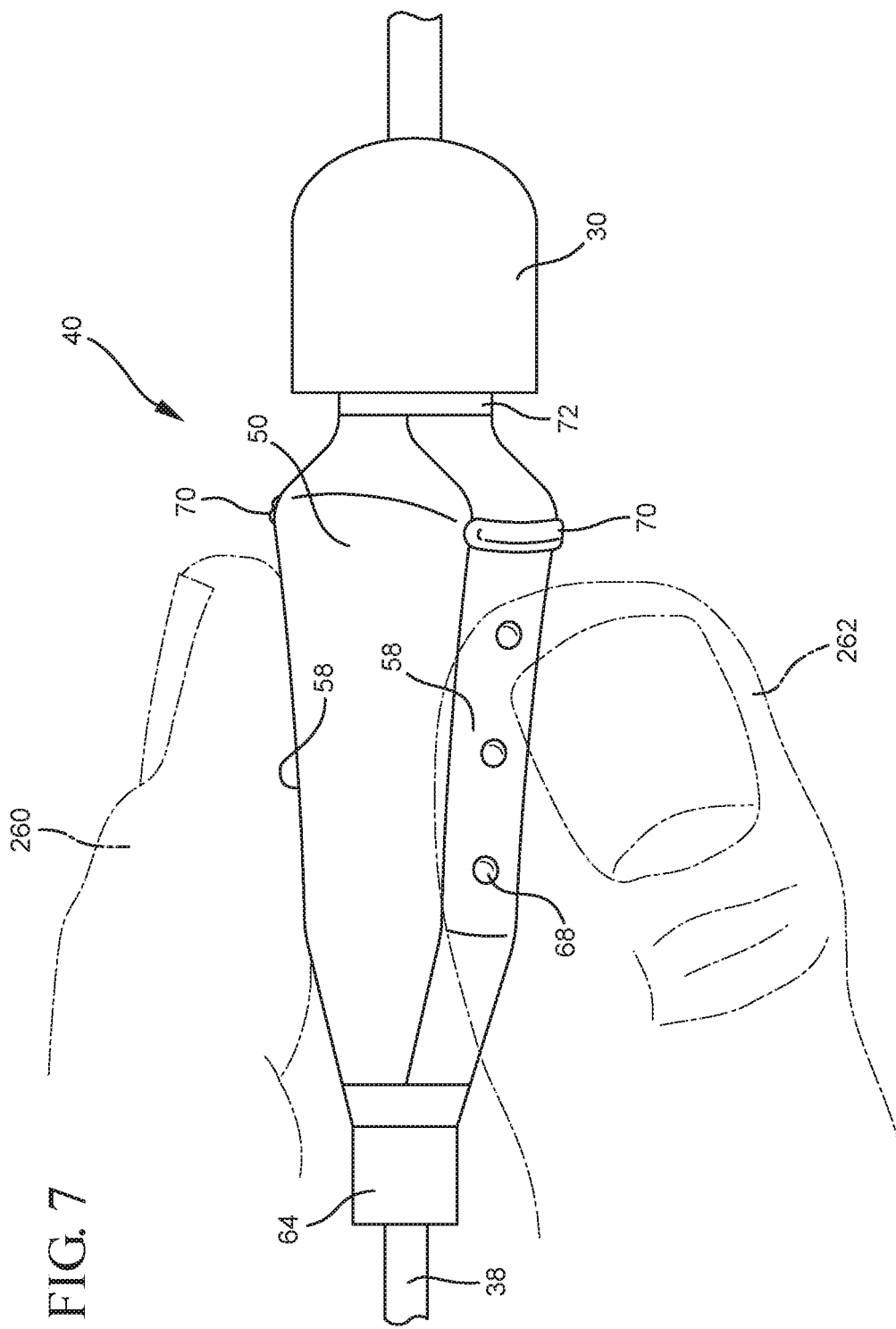
FIG. 7 is a perspective view of a luer connector held with a user's fingers in accordance with representative embodiments of the present invention.

Additionally or alternatively to the larger sizing of the luer connector 40, improved gripping of the luer connector 40 can be accomplished by including a flexible material 64 on at least a portion of the outer surface of the connector body 41. The flexible material 64 can be disposed on include at least a portion of the grip portion 50, the ergonomic finger indent 58, and or the distal end 54 (as shown in FIG. 7). In some embodiments, the flexible material is compressible, spongy, has a high friction coefficient, and/or is elastic. In some instanced, the flexible material 64 is a thermoplastic elastomer (TPE). Alternatively, a compressible material, spongy material, semi-flexible material, or elastic material replaces the flexible material 64.

In some embodiments, the luer connector 40 includes both a flexible material 64 and a rigid or semi-rigid material (herein referred to as a rigid material) 66. In some embodiments, the rigid material 66 form part of the connecting portions of the luer connector, which are generally located on the distal end 54 and the proximal end 52, as shown. In some configurations, the flexible material 64 and the rigid material 66 of the luer connector 40 are manufactured in an overmold process, which manufactures the rigid material 66 and the flexible material 64 over the rigid material 66. In some configurations, the rigid material 66 includes a polyester copolyester or other similar material. The rigid material 66 can form a skeleton or structure of the luer connector, while the flexible material 64 forms an exterior surface that can improve gripping of the luer connector 40. Thus, the rigid material 66 can span, at least approximately, between the distal end 54 and the proximal end 52 of the luer connector. In some embodiments, the rigid material 66 extends through the flexible material 64 to form gripping features 68 and 70. In other embodiments, the gripping features 68 and 70 are formed of a third material that can be flexible, semi-flexible, rigid, or semi-rigid. In embodiments where the connector body 41 includes two separate materials, the variation between the two materials can provide improved gripping. For instance, the two materials may react differently to bare skin, sterile gloves, wet hands/gloves, etc. The combination of the two materials can synergistically provide improved gripping in many common situations and circumstances.

In some embodiments, the luer connector 40 can include one or more gripping features 68. The gripping feature can include protrusions 68 or texture formed in the connector body 41. The gripping features 68 can include any feature with a different hardness, texture, and tackiness than the exterior surface of the connector body 41. The grip portion 50 of the luer connector 40 is gripped by a user in the process of connecting the luer connector fitting 72 to a corresponding feature (not shown) of a separate device, such as the coupler 30 of FIGS. 1 to 3 and 7. Since the quality of the connection between these devices is dependent upon the clinician's ability to twist the two together, the luer connector 40 should be adequately gripped. Thus, in some embodiments, one or more gripping features 68 protrude from the outer surface of the flexible material 64.

In some embodiments, one or more gripping features 68 are disposed on a natural gripping surface 42 that has an opposing ergonomic finger indent 58 that comfortably provides a curvature that approximately matches the shape of a clinician's fingers. This natural gripping surface 64 provides the clinician with a natural location to place his or her fingers when gripping the luer connector body 41. In some instances, the natural gripping surface 64 does not have gripping features 68, but has a texture, other feature, or no gripping features 68. The one or more gripping features 70 can be disposed on other portions of the luer connector 40 as well. The gripping features 70 can have various configurations that facilitate a comfortable, grippable luer connector 40.

The larger grip portion 50 can assist practitioners to fully engage the luer connector 40 and thus avoid the problem of incompletely connecting the connection. When twisting the luer connector 40 to a completely engaged position, the resistance to engagement can grow as the luer connector 40 is twisted. Clinical observations have shown that clinicians commonly fail to completely engage the luer connector 40. This failure is problematic with high pressure injections system, in which an incompletely engages luer lock can leak, disengage, and/or result in pressure loss. A larger luer connector 40 can be easier to grip and twist and can provide more leverage to a clinician so that the luer connector 40 can be twisted more easily and completely. This size can thus result in fewer system failures.

Figure 6:
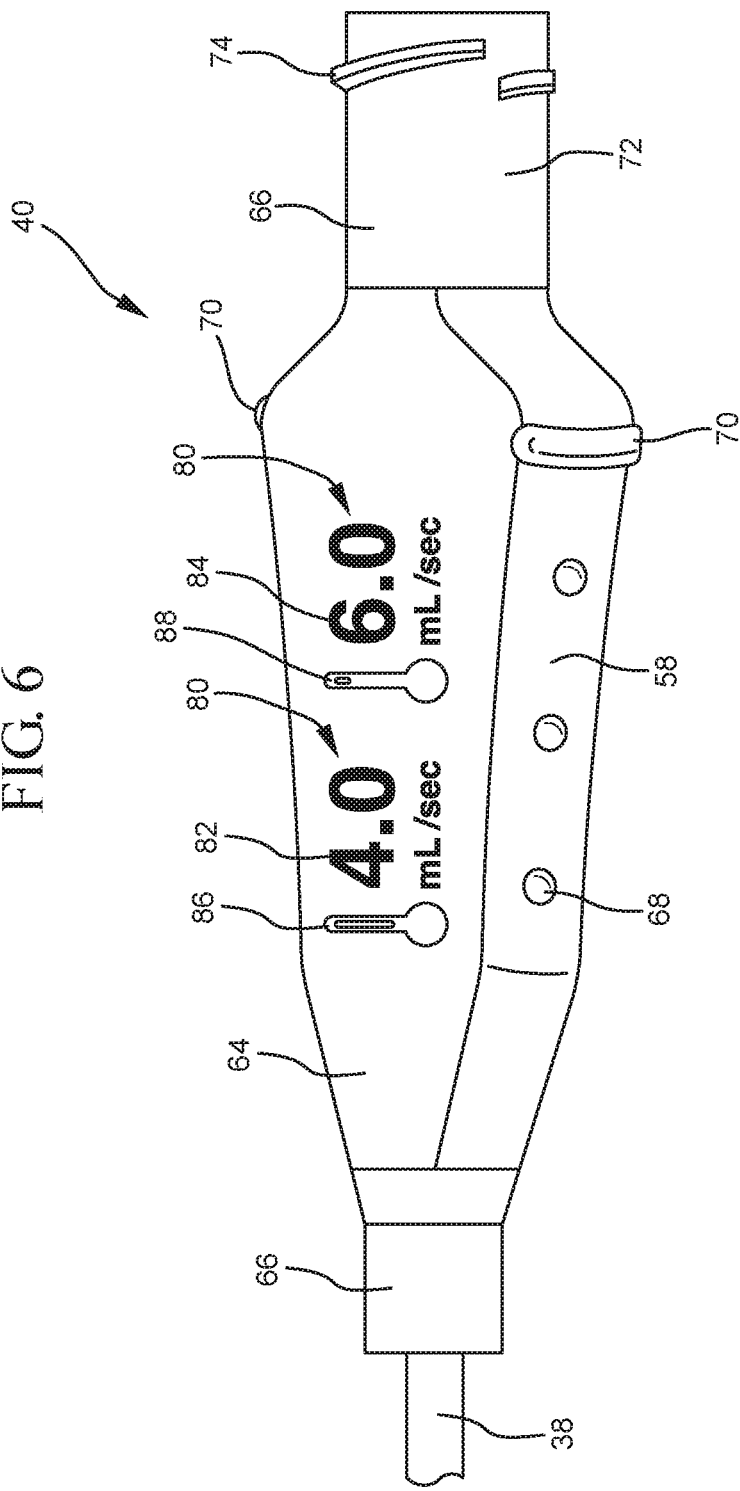
FIG. 6 is a perspective view of a luer connector having a label in accordance with representative embodiments of the present invention.

As shown in FIG. 6, the larger sizing of the luer connector 40 can provide an increased surface area onto which a label can be provided. A label 80 can present information to the practitioner each time he or she looks at the luer connector 40 to connect it to another device. In some instance, the label 80 can include product specifications, including the maximum flow rate 82, 84 for which the luer connector and/or a down line catheter adapter are configured. As explained above, in some instances, product specifications are included in product literature, which is not generally present to a practitioner when using the device. This information, even if it is critical, can be forgotten temporarily or permanently by a practitioner. By disposing the label 80 in this accessible location, it can remind the practitioner of the labeled information each time the luer connector 40 is used or observed.

The size of the luer connector 40 can provide enough surface area for label having a font size of 10 point font or larger to be written thereon. For instance, a label indicating maximum flow rates can have a font size of 12 point font. The 12 point font may be readable by the average clinician using the luer connector 40.

In a non-limiting example, as shown in FIG. 6, the label 80 includes the maximum flow rates based on the temperature of the infusant. In some configurations, depictions of a thermometer 84, 86 can indicate high or low temperature rates. As shown, a depiction of thermometer 86 with a low level of mercury can assist to designate the low temperature rate. A depiction of thermometer 84 with a high level of mercury can assist to designate the high temperature rate. Additionally or alternatively, the low temperature rate can be made with a blue text, blue commonly indicating a cool or cold temperature. And, the high temperature rate can be made with a red text, red commonly indicating a warm or hot temperature. These text, symbols, and colors can provide clearly visible information and/or reminders to a clinician of product specifications or other important product information, which is presented at the time it is needed.

In some configurations, a portion or all of the luer connector 40 is colored purple. This portion can be the flexible material 64, the rigid material 66, the grip portion 50, and/or the label 80. A survey of power injector clinicians has revealed that clinicians relate the color purple to power injection devices over other colors. Accordingly, a purple-colored luer connector 40 can be recognized, even at a distance, as the luer connector 40 of a power injector device. This purple color can provide rapid recognition of a luer connector 40 even when it is located across a room or located with various other devices.

FIG. 7 illustrates the luer port 40 in use. As shown, when two fingers 260, 262 grasp the luer port 40 on the ergonomic finger indents 58, the user's finger are spaced apart farther than in prior art luer ports, such as that shown in FIGS. 1 to 3, which provides additional leverage to the user's fingers. Furthermore, the user's fingers grip at least some of the softer material 64, which is more comfortable to grip and can provide increased surface friction for a tighter grip. The larger width 62 and lengths 55, 56 of the luer port 40 also locate the user's finger away from the luer connector fitting 72, which can prevent the user's fingers from blocking the advancement of the coupler 30 onto the luer port 40 and remove the likelihood that the user take this as an indication that the interconnection is sufficiently made. The profile change between the luer connector fitting 72 and the grip portion 50 also naturally indicate that the user should not grip the luer connector fitting 72, as well as provide a naturally barrier that make gripping the luer connector fitting 72 difficult. This profile change also prevents the user's fingers from choking up by gripping the proximal most end of the gripping body portion 50, which would feel unnatural and incorrect. In some configurations, a grip shield 70 is interposed between the grip portion 50 of the connector body 41 and the luer connector fitting 72. In some embodiments, the grip shield 70 protrudes outwardly from the surface of the connector body 41 and physically limits the placement of a finger on or proximal the grip shield 70. In other embodiments, the grip shield 70 protrudes outwardly, but does not physically limit the placement of the finger, but provides a tactile indication of the edge of the grip portion 50. Thus, the grip shield and/or the ergonomic indent 58 can provide an indication to the user of the correct finger position on the connector body 41 in order to increase the likelihood of a proper connection between the luer port 40 and the coupler 30.

Figure 8:
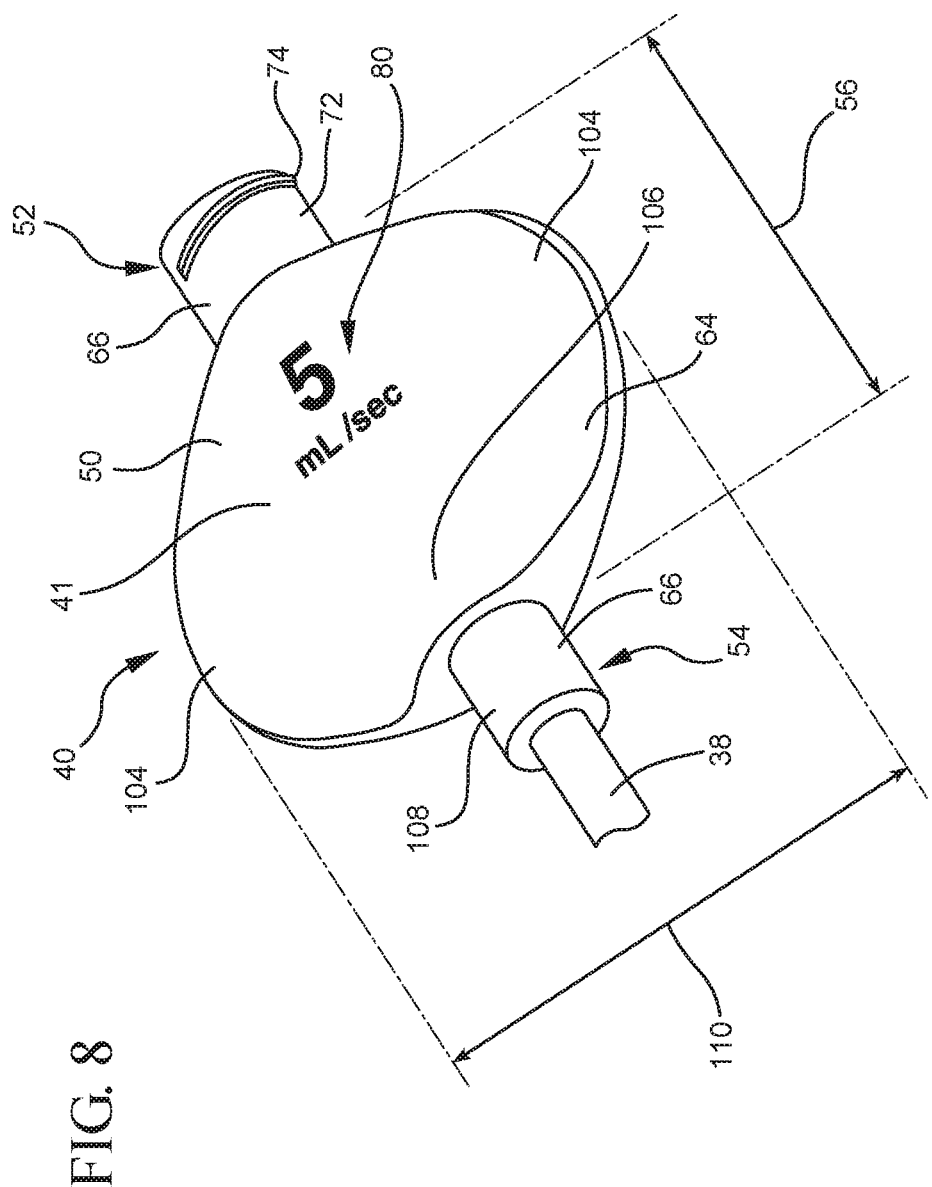
FIG. 8 is a perspective view of another luer connector having a label in accordance with representative embodiments of the present invention.

FIG. 8 illustrates another embodiment of a luer port 40. As shown, the connector body 41 of the luer port 40 includes a luer connector fitting 72 on its proximal end and a distal connector portion 108 on its distal end. Between the proximal and the distal ends is a disk-shaped grip portion 50 that includes wing portions 104 extending out from a central portion 106. This grip portion 50 has wing portions 104 having a width or wing span 110 and a length 112. In some configurations, the width 110 is approximately the same as the length 56 so that the grip portion 50 is substantially circular. In other configurations, the width 110 is not the same dimensions as the length 56. In some instances the length 56 of the grip portion 50 is between about 0.6 and 2.0 inches. In other embodiments, the length 56 of the grip portion 50 of the connector body 41 is between about 0.8 and 1.8 inches. In still other embodiments, the length 56 of the grip portion 50 of the connector body 41 is between about 1.1 and 1.4 inches. Additionally, in some configurations, the length 55 of the entire luer connector 40 is between about 1.3 and 1.8 inches. In other configurations, the length 55 of the entire luer connector 40 is between about 1.5 and 1.6 inches.

Similarly, in some instances the width 110 of the grip portion 50 is between about 0.6 and 2.0 inches. In other embodiments, the width 110 of the grip portion 50 of the connector body 41 is between about 0.8 and 1.8 inches. In still other embodiments, the width 110 of the grip portion 50 of the connector body 41 is between about 1.1 and 1.4 inches.

The luer port 40 can provide a user with sufficient leverage to completely twist the luer port 40 to a fully connected position. As shown, in some embodiments, the central portion 106 is thicker than the distal connector 108 and/or the luer connector fitting 72. This permits the user's fingers to naturally stay away from the luer connector fitting 72 particularly while the user is twisting the luer port 40 to a connected position. As the user grips the central portion and/or the wing portions 104, the user's fingers can press against the wing portions 104 to gain additional leverage to more easily twist the luer port 40.

In some instances, at least a portion of the grip portion 50 and/or the distal connector portion 108 are made of a flexible material 64 that facilitates gripping of the grip portion 50. And in some instances, one or more gripping features 68 are disposed on the grip portion 50. These features and materials can provide increased comfort, grip, and leverage to the user.

FIG. 9 illustrates another embodiment of a vascular infusion system 20. The vascular infusion system 20 includes a peripheral intravenous catheter adapter 34 with a short or truncated catheter 36 and flap 120. As shown, a label 80 is placed on the flap 120. This label 80 can provide information to clinicians introducing the truncated catheter 36 into a patient. In this prominent position, it is likely to catch the eye and the attention of the clinician and result in the clinician complying with any instructions or specifications on the label 80. This label can include the same type of information as included on the label 80 of FIG. 6. This label can be included in addition to or alternatively to that on the luer connector 40. When a label 80 is placed on both the peripheral intravenous catheter adapter 34 and the luer connector 40, the two or more labels can provide the same or different information.

From the foregoing it can be seen that the luer connector 40 is shaped and sized to be ergonomic and easily manageable such that it facilitates greater leverage and improved connections. The luer connector's label 80 can provide visible text that indicates the product specifications that are useful or critical to the operation of a down line device. Since clinicians must connect the connector with its down line catheter adapter to the power injector, the connector provides an appropriate location to label the maximum flow rates of the catheter adapter. Providing this information to clinician can encourage proper infusant rates, which will result in fewer complications involving instruments and patient injuries.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A vascular access device comprising:
   a catheter adapter;
   a catheter that extends from the catheter adapter;
   a luer lock connector;

IV tubing having a first end and a second end, the first end being secured within the luer lock connector and the second end being secured within the catheter adapter thereby forming a fluid pathway for injecting a fluid through the luer lock connecter, the IV tubing, the catheter adapter, and the catheter and into a patient's vasculature; and at least one indication of a maximum flow rate of an infusant for which the vascular access device is configured, the at least one indication being positioned on a surface of the catheter adapter, wherein the at least one indication comprises a first indication of a first maximum flow rate when the infusant is at a first temperature and a second indication of a second maximum flow rate when the infusant is at a second temperature, wherein the luer lock connector comprises:
- a connector body having a distal end, a proximal end, and a gripping portion between the distal end and the proximal end, the first end of the IV tubing being secured within the distal end of the connector body;
- a substantially flexible material disposed on at least the outer surface of the gripping portion of the connector body; and
- a luer connector fitting disposed on the proximal end of the body, the luer connector fitting having an outer diameter less than a maximum exterior thickness of the gripping portion of the connector body.

2. The vascular access device of claim 1, wherein the catheter adapter includes a flap, wherein the first indication or the second indication is positioned on the flap.

3. The vascular access device of claim 1, wherein the catheter adapter includes a first flap and a second flap, wherein the first indication is positioned on a surface of the first flap and the second indication is positioned on a surface of the second flap.

4. The vascular access device of claim 3, wherein the catheter adapter includes a peripheral intravenous catheter adapter, wherein the catheter is a truncated catheter.

5. The vascular access device of claim 1, wherein the at least one indication is in 12 point font or larger.

6. The vascular access device of claim 1, further comprising a substantially rigid material forming an inner portion of the connector body and forming the luer connector fitting.

7. The vascular access device of claim 6, wherein the maximum exterior thickness of the gripping portion is greater than or equal to 0.2 inches, and wherein the connector body has a length greater than or equal to 1.1 inches, and wherein the connector body forms a single port connector.

8. The vascular access device of claim 7, wherein the outer surface of the gripping portion is substantially disk-shaped.

9. The vascular access device of claim 7, wherein the gripping portion of the connector body includes ergonomic grip indents on opposing sides of the connector body.

10. The vascular access device of claim 9, wherein the ergonomic grip indents include one or more gripping features.

11. The vascular access device of claim 9, further comprising a grip shield interposed between the gripping portion and the luer connector fitting.

12. The vascular access device of claim 9, wherein the outer surface of the gripping portion of the connector body tapers from a larger proximal portion to a smaller distal portion.

13. A vascular access device comprising:
a catheter adapter;
a catheter that extends from the catheter adapter;
a luer lock connector;
IV tubing having a first end and a second end, the first end being secured within the luer lock connector and the second end being secured within the catheter adapter thereby forming a fluid pathway for injecting a fluid through the luer lock connecter, the IV tubing, the catheter adapter, and the catheter and into a patient's vasculature;
a first indication of a first maximum flow rate of an infusant for which the vascular access device is configured, the first maximum flow rate being based on a first temperature of the infusant; and
a second indication of a second maximum flow rate of the infusant for which the vascular access device is configured, the second maximum flow rate being based on a second temperature of the infusant,
wherein the luer lock connector comprises:
- a connector body having a distal end, a proximal end, and a gripping portion between the distal end and the proximal end, the connector body forming a single port connector, the first end of the IV tubing being secured within the distal end of the connector body;
- a luer connector fitting disposed on the proximal end of the body;
- a substantially rigid material forming the single port of the connector body and an inner portion of the connector body; and
- a flexible material forming at least an outer portion of the gripping portion of the connector body.

14. The vascular access device of claim 13, wherein the flexible material is molded over the rigid material.

15. The vascular access device of claim 13, wherein the gripping portion has a maximum thickness greater than the outer thickness of the luer connector fitting, the maximum thickness being equal to or greater than 0.2 inches, the gripping portion further having a maximum length equal to or greater than 1.1 inches.

16. The vascular access device of claim 13, wherein the gripping portion of the connector body includes ergonomic grip indents on opposing sides of the connector body.

17. The vascular access device of claim 16, further comprising a grip shield interposed between the gripping portion and the luer connector fitting.

18. A vascular access device comprising:
a catheter adapter;
a catheter that extends from the catheter adapter;
a luer lock connector;
IV tubing having a first end and a second end, the first end being secured within the luer lock connector and the second end being secured within the catheter adapter thereby forming a fluid pathway for injecting a fluid through the luer lock connecter, the IV tubing, the catheter adapter, and the catheter and into a patient's vasculature;
a first indication of a first maximum flow rate and a corresponding representation of a first temperature of an infusant for which the vascular access device is configured; and
a second indication of a second maximum flow rate and a corresponding representation of a second temperature of the infusant for which the vascular access device is configured, wherein the luer lock connector comprises:
- a connector body having a distal end, a proximal end, and a gripping portion between the distal end and the proximal end, the connector body forming a single port connector, the first end of the IV tubing being secured within the distal end of the connector body;
- a luer connector fitting disposed on the proximal end of the body, the luer connector fitting having an outer diameter less than a maximum exterior thickness of the gripping portion of the connector body, the maximum thickness being equal to or greater than 0.2 inches, the gripping portion further having a maximum length equal to or greater than 1.1 inches;
- a grip shield interposed between the gripping portion of the connector body and the luer connector fitting;
- a first material forming the single port connector of the connector body and an inner portion of the connector body, the first material being substantially rigid; and
- a second material forming at least an outer portion of the gripping portion of the connector body, the second material being compressible.

19. The vascular access device of claim 18, wherein the at least one indication is in 12 point font or larger.

20. The vascular access device of claim 18, wherein the outer surface of the gripping portion of the connector body tapers from a larger proximal portion to a smaller distal portion.

* * * * *